US011612525B2

(12) United States Patent
Sillerström et al.

(10) Patent No.: US 11,612,525 B2
(45) Date of Patent: *Mar. 28, 2023

(54) ABSORBENT ARTICLE AND METHOD FOR MANUFACTURING AN ABSORBENT ARTICLE

(71) Applicant: Essity Hygiene and Health Aktiebolag, Gothenburg (SE)

(72) Inventors: Filip Sillerström, Gothenburg (SE); Per Camén, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 456 days.

This patent is subject to a terminal disclaimer.

(21) Appl. No.: 16/758,666

(22) PCT Filed: Dec. 21, 2017

(86) PCT No.: PCT/SE2017/000055
§ 371 (c)(1),
(2) Date: Apr. 23, 2020

(87) PCT Pub. No.: WO2019/125232
PCT Pub. Date: Jun. 27, 2019

(65) Prior Publication Data
US 2020/0352799 A1    Nov. 12, 2020

(51) Int. Cl.
A61F 13/511    (2006.01)
A61F 13/532    (2006.01)
(Continued)

(52) U.S. Cl.
CPC ...... A61F 13/539 (2013.01); A61F 13/15203 (2013.01); A61F 13/15739 (2013.01);
(Continued)

(58) Field of Classification Search
CPC .......... A61F 13/15203; A61F 13/15577; A61F 13/15617; A61F 13/15634;
(Continued)

(56) References Cited

U.S. PATENT DOCUMENTS 5,037,415 A    8/1991  Leroy et al.
5,330,456 A    7/1994  Robinson
(Continued)

FOREIGN PATENT DOCUMENTS

CN    1206341 A    1/1999
CN    1642501 A    7/2005
(Continued)

OTHER PUBLICATIONS

Extended European Search Report dated Aug. 4, 2021, issued by the European Patent Office in corresponding European Application No. 17935663.9-1102, (9 pages).
(Continued)

Primary Examiner — Michael A Tolin
(74) Attorney, Agent, or Firm — Buchanan Ingersoll & Rooney P.C.

(57) ABSTRACT

An absorbent article including an absorbent core sandwiched between a liquid-permeable topsheet and a liquid-impermeable backsheet, wherein the absorbent core includes an absorbent component enclosed by a core cover including an upper side and a lower side, and a sealing arrangement for joining the upper and lower sides and including two channel sealings in the crotch portion defining a first channel sealing width and a second channel sealing width. The channel sealings are formed by thermo and/or mechanical welding pattern including a plurality of welding spots being arranged in the form of a first row along the longitudinal axis in which each welding spot extends along a first axis, and a second row along the longitudinal axis in which each welding spot
(Continued)

extends along a second axis, the first axis and second axis defining a first angle in relation to each other.

17 Claims, 4 Drawing Sheets

(51) Int. Cl.
| | | |
|---|---|---|
| *A61F 13/537* | (2006.01) | |
| *A61F 13/49* | (2006.01) | |
| *A61F 13/539* | (2006.01) | |
| *A61F 13/15* | (2006.01) | |
| *B32B 37/00* | (2006.01) | |
| *A61F 13/53* | (2006.01) | |

(52) U.S. Cl.
CPC ........ *A61F 13/49* (2013.01); *A61F 13/51113* (2013.01); *A61F 13/5323* (2013.01); *B32B 37/0084* (2013.01); *A61F 2013/15406* (2013.01); *A61F 2013/15886* (2013.01); *A61F 2013/530007* (2013.01); *A61F 2013/5395* (2013.01); *A61F 2013/530481* (2013.01); *A61F 2013/53778* (2013.01); *A61F 2013/53991* (2013.01)

(58) Field of Classification Search
CPC .......... A61F 13/15658; A61F 13/15699; A61F 13/15739; A61F 13/15804; A61F 13/49; A61F 13/49001; A61F 13/51113; A61F 13/532; A61F 13/5323; A61F 13/534; A61F 13/53708; A61F 13/539; A61F 2013/15406; A61F 2013/15861; A61F 2013/15869; A61F 2013/15878; A61F 2013/15886; A61F 2013/15902; A61F 2013/530007; A61F 2013/530481; A61F 2013/530868; A61F 2013/53778; A61F 2013/5395; A61F 2013/53991; B32B 37/0084

See application file for complete search history.

(56) References Cited

U.S. PATENT DOCUMENTS

| | | | |
|---|---|---|---|
| 5,354,289 A | 10/1994 | Mitchell et al. | |
| 5,622,734 A | 4/1997 | Clark et al. | |
| 6,102,900 A | 8/2000 | Roessler et al. | |
| 6,231,554 B1 | 5/2001 | Menard | |
| 6,423,046 B1 | 7/2002 | Fujioka et al. | |
| 6,563,013 B1 | 5/2003 | Murata | |
| 6,573,422 B1 | 6/2003 | Rosenfeld et al. | |
| 9,132,046 B2 | 9/2015 | Glaug et al. | |
| 9,232,046 B2 | 1/2016 | Naqvi | |
| 9,974,698 B2 | 5/2018 | Jackels | |
| 10,071,000 B2 | 9/2018 | Umemoto et al. | |
| 10,149,788 B2 | 12/2018 | Kreuzer et al. | |
| 10,561,546 B2 | 2/2020 | Rosati et al. | |
| 10,806,642 B2 | 10/2020 | Tagomori et al. | |
| 11,007,095 B2* | 5/2021 | Sillerström | A61F 13/42 |
| 11,229,561 B2* | 1/2022 | Sillerström | A61F 13/49 |
| 2001/0014797 A1 | 8/2001 | Suzuki et al. | |
| 2002/0007165 A1 | 1/2002 | Proglhof et al. | |
| 2002/0032427 A1 | 3/2002 | Schmitz et al. | |
| 2002/0065498 A1 | 5/2002 | Ohashi et al. | |
| 2003/0060791 A1 | 3/2003 | Drevik | |
| 2003/0134559 A1 | 7/2003 | Delzer et al. | |
| 2004/0127871 A1 | 7/2004 | Odorzynski et al. | |
| 2004/0138633 A1 | 7/2004 | Mishima et al. | |
| 2004/0243078 A1 | 12/2004 | Guidotti et al. | |
| 2006/0229579 A1 | 10/2006 | Wahlstrom et al. | |
| 2006/0276767 A1 | 12/2006 | Ueminami et al. | |
| 2007/0093164 A1 | 4/2007 | Nakaoka | |
| 2007/0142802 A1 | 6/2007 | Suzuki | |
| 2008/0119810 A1 | 5/2008 | Kuroda et al. | |
| 2008/0132864 A1 | 6/2008 | Lawson et al. | |
| 2008/0215024 A1 | 9/2008 | Diehl et al. | |
| 2008/0300561 A1 | 12/2008 | Stridfeldt et al. | |
| 2008/0300564 A1 | 12/2008 | Bogren et al. | |
| 2009/0036854 A1 | 2/2009 | Guidotti et al. | |
| 2009/0082744 A1 | 3/2009 | Hakansson et al. | |
| 2009/0088718 A1 | 4/2009 | Toyoshima et al. | |
| 2009/0270825 A1 | 10/2009 | Wciorka et al. | |
| 2009/0292266 A1 | 11/2009 | Back | |
| 2010/0030173 A1 | 2/2010 | Song et al. | |
| 2010/0168700 A1 | 7/2010 | Schmidt et al. | |
| 2010/0168701 A1 | 7/2010 | Schmidt et al. | |
| 2010/0249743 A1 | 9/2010 | Takino | |
| 2010/0262099 A1 | 10/2010 | Klofta | |
| 2010/0268183 A1 | 10/2010 | Een | |
| 2011/0004178 A1 | 1/2011 | Fernkvist et al. | |
| 2011/0046590 A1 | 2/2011 | Mukai et al. | |
| 2011/0196327 A1* | 8/2011 | Chhabra | A61F 13/4753 604/385.101 |
| 2011/0250413 A1 | 10/2011 | Lu et al. | |
| 2012/0143164 A1 | 6/2012 | Frank et al. | |
| 2012/0296301 A1 | 11/2012 | Lawson et al. | |
| 2012/0312491 A1 | 12/2012 | Jackels et al. | |
| 2012/0316526 A1 | 12/2012 | Rosati et al. | |
| 2012/0316528 A1 | 12/2012 | Kreuzer et al. | |
| 2012/0316529 A1 | 12/2012 | Kreuzer et al. | |
| 2012/0316530 A1 | 12/2012 | Armstrong-ostle et al. | |
| 2012/0323195 A1 | 12/2012 | Ehrnsperger et al. | |
| 2012/0325408 A1 | 12/2012 | Hundorf et al. | |
| 2013/0138070 A1 | 5/2013 | Drevik | |
| 2013/0231622 A1 | 9/2013 | Dieringer et al. | |
| 2014/0005625 A1 | 1/2014 | Wirtz et al. | |
| 2014/0027066 A1 | 1/2014 | Jackels et al. | |
| 2014/0088535 A1 | 3/2014 | Xu et al. | |
| 2014/0163500 A1 | 6/2014 | Roe et al. | |
| 2014/0163503 A1 | 6/2014 | Arizti et al. | |
| 2014/0163506 A1 | 6/2014 | Roe et al. | |
| 2014/0163511 A1 | 6/2014 | Roe et al. | |
| 2014/0276503 A1 | 9/2014 | Sheldon et al. | |
| 2014/0303583 A1 | 10/2014 | Berrizbeitia | |
| 2014/0324007 A1 | 10/2014 | Hundorf et al. | |
| 2014/0324008 A1 | 10/2014 | Hundorf et al. | |
| 2014/0371701 A1 | 12/2014 | Bianchi et al. | |
| 2015/0005729 A1 | 1/2015 | Nakao et al. | |
| 2015/0032073 A1 | 1/2015 | Noda et al. | |
| 2015/0038931 A1 | 2/2015 | Kreuzer et al. | |
| 2015/0051568 A1 | 2/2015 | Sakaguchi et al. | |
| 2015/0065975 A1* | 3/2015 | Roe | A61F 13/49001 604/374 |
| 2015/0065976 A1 | 3/2015 | Roe et al. | |
| 2015/0080821 A1 | 3/2015 | Peri et al. | |
| 2015/0148766 A1 | 5/2015 | Nakakado | |
| 2015/0173968 A1 | 6/2015 | Joseph | |
| 2015/0245954 A1 | 9/2015 | Varga et al. | |
| 2015/0311351 A1 | 10/2015 | Seko et al. | |
| 2015/0366725 A1 | 12/2015 | Toda et al. | |
| 2015/0374562 A1 | 12/2015 | Hippe et al. | |
| 2016/0058630 A1 | 3/2016 | Roe et al. | |
| 2016/0058632 A1 | 3/2016 | Lawson et al. | |
| 2016/0081862 A1 | 3/2016 | Mason et al. | |
| 2016/0206482 A1 | 7/2016 | Nishikawa et al. | |
| 2016/0206485 A1 | 7/2016 | Seitz et al. | |
| 2016/0235595 A1 | 8/2016 | Ehrnsperger et al. | |
| 2016/0235596 A1 | 8/2016 | Ehrnsperger et al. | |
| 2016/0235604 A1 | 8/2016 | Ehrnsperger et al. | |
| 2016/0270971 A1 | 9/2016 | Raycheck et al. | |
| 2016/0270982 A1 | 9/2016 | Raycheck et al. | |
| 2016/0270986 A1 | 9/2016 | Stiehl et al. | |
| 2016/0270987 A1 | 9/2016 | Stiehl et al. | |
| 2016/0278986 A1 | 9/2016 | Gross et al. | |
| 2016/0310330 A1 | 10/2016 | Knos et al. | |
| 2016/0331600 A1 | 11/2016 | Polidori et al. | |
| 2016/0331602 A1 | 11/2016 | Bianchi et al. | |
| 2016/0346136 A1 | 12/2016 | Strasemeier et al. | |
| 2017/0057157 A1 | 3/2017 | Lebowitz | |
| 2017/0079853 A1* | 3/2017 | Willhaus | A61F 13/539 |
| 2017/0079857 A1 | 3/2017 | Willhaus et al. | |
| 2017/0119594 A1 | 5/2017 | Bewick-Sonntag et al. | |

(56) References Cited

U.S. PATENT DOCUMENTS

| | | |
|---|---|---|
| 2017/0172810 A1 | 6/2017 | Van De Maele |
| 2017/0252226 A1 | 9/2017 | Arizti et al. |
| 2018/0021187 A1 | 1/2018 | Nishikawa et al. |
| 2018/0049924 A1 | 2/2018 | Van De Maele |
| 2018/0049925 A1 | 2/2018 | Van De Maele |
| 2019/0038477 A1 | 2/2019 | Jackels et al. |
| 2020/0078229 A1 | 3/2020 | Van Ingelgem et al. |
| 2020/0337909 A1 | 10/2020 | Sillerström et al. |
| 2021/0177671 A1 | 6/2021 | Sillerström et al. |
| 2021/0186772 A1 | 6/2021 | Sillerström et al. |

FOREIGN PATENT DOCUMENTS

| | | |
|---|---|---|
| CN | 101132751 A | 2/2008 |
| CN | 101312699 A | 11/2008 |
| CN | 101340873 A | 1/2009 |
| CN | 101484296 A | 7/2009 |
| CN | 101677892 A | 3/2010 |
| CN | 102006846 A | 4/2011 |
| CN | 102770592 A | 11/2012 |
| CN | 103596534 A | 2/2014 |
| CN | 103607990 A | 2/2014 |
| CN | 104039288 A | 9/2014 |
| CN | 203988675 U | 12/2014 |
| CN | 104379102 A | 2/2015 |
| CN | 104837458 A | 8/2015 |
| CN | 204671400 U | 9/2015 |
| CN | 105062444 A | 11/2015 |
| CN | 105473113 A | 4/2016 |
| CN | 105816277 A | 8/2016 |
| CN | 106137542 A | 11/2016 |
| CN | 107249529 A | 10/2017 |
| CN | 107405240 A | 11/2017 |
| CO | 4230216 A1 | 10/1995 |
| CO | 4290405 A1 | 4/1996 |
| CO | 4480014 A1 | 7/1997 |
| CO | 5070616 A1 | 8/2001 |
| CO | 5180618 A1 | 7/2002 |
| CO | 11012996 | 12/2011 |
| DE | 29513199 U1 | 2/1996 |
| DE | 202012013564 U | 12/2017 |
| DE | 202012013571 U1 | 12/2017 |
| DE | 202013012614 U1 | 12/2017 |
| DE | 202013012616 U1 | 12/2017 |
| DE | 202013012617 U1 | 12/2017 |
| DE | 202017005496 U1 | 1/2018 |
| DE | 202014011155 U1 | 3/2018 |
| DE | 202017005950 U1 | 4/2018 |
| DE | 202017005952 U1 | 4/2018 |
| DE | 202017005956 U1 | 4/2018 |
| EP | 0813850 A2 | 12/1997 |
| EP | 0958801 A1 | 11/1999 |
| EP | 1110528 A2 | 6/2001 |
| EP | 1 116 479 A2 | 7/2001 |
| EP | 1880700 A1 | 1/2008 |
| EP | 1679055 B1 | 4/2010 |
| EP | 2444046 A1 | 4/2012 |
| EP | 2740449 A1 | 6/2014 |
| EP | 2740450 A1 | 6/2014 |
| EP | 2740452 A1 | 6/2014 |
| EP | 2886092 A1 | 6/2015 |
| EP | 2886093 A1 | 6/2015 |
| EP | 2905000 A1 | 8/2015 |
| EP | 2949299 A1 | 12/2015 |
| EP | 2949300 A1 | 12/2015 |
| EP | 2949301 A1 | 12/2015 |
| EP | 2949302 A1 | 12/2015 |
| EP | 2979671 A1 | 2/2016 |
| EP | 2717823 B1 | 5/2016 |
| EP | 3058915 A1 | 8/2016 |
| EP | 3058918 A1 | 8/2016 |
| EP | 3111903 A1 | 1/2017 |
| EP | 3167858 A1 | 5/2017 |
| EP | 3167859 A1 | 5/2017 |
| EP | 3238676 A1 | 11/2017 |
| EP | 3338751 A1 | 6/2018 |
| EP | 3348246 A1 | 7/2018 |
| EP | 3403626 A1 | 11/2018 |
| EP | 3403632 A1 | 11/2018 |
| EP | 3453368 A1 | 3/2019 |
| FR | 2604867 A1 | 4/1988 |
| GB | 1171116 A | 11/1969 |
| GB | 2 510 665 A | 8/2014 |
| GB | 2518174 A | 3/2015 |
| JP | 2003-093445 A | 4/2003 |
| JP | 3 811 000 B2 | 8/2006 |
| JP | 2007-195792 A | 8/2007 |
| JP | 2008119081 A | 5/2008 |
| JP | 2009-018183 A | 1/2009 |
| JP | 2009-517172 A | 4/2009 |
| JP | 2011125360 A | 6/2011 |
| JP | 2012-513842 A | 6/2012 |
| JP | 2013-013683 A | 1/2013 |
| JP | 2013102888 A | 5/2013 |
| JP | 2014-028492 A | 2/2014 |
| JP | 2014-090724 A | 5/2014 |
| JP | 2014-515983 A | 7/2014 |
| JP | 2014204754 A | 10/2014 |
| JP | 2014-90724 A | 11/2015 |
| JP | 3201606 U | 11/2015 |
| JP | 2016514570 A | 5/2016 |
| JP | 2016112359 A | 6/2016 |
| JP | 2016112404 A | 6/2016 |
| JP | 5946517 B1 | 7/2016 |
| JP | 2016-174741 A | 10/2016 |
| JP | 2017-051596 A1 | 3/2017 |
| JP | 2017-221722 A | 12/2017 |
| JP | 6334729 B2 | 5/2018 |
| NC | 2016/0005094 | 3/2017 |
| RU | 2260414 C2 | 9/2005 |
| RU | 2379014 C2 | 1/2010 |
| RU | 2519567 C2 | 6/2014 |
| WO | 98/24390 A2 | 6/1998 |
| WO | 0217842 A2 | 3/2002 |
| WO | 0217843 A2 | 3/2002 |
| WO | 02056812 A2 | 7/2002 |
| WO | 2002/091975 A1 | 11/2002 |
| WO | 2004006818 A1 | 1/2004 |
| WO | 2005065611 A1 | 7/2005 |
| WO | 2007046974 A1 | 4/2007 |
| WO | 2009001711 A1 | 12/2008 |
| WO | 2009128757 A1 | 10/2009 |
| WO | 2010/015053 A1 | 2/2010 |
| WO | 2010/078302 A1 | 7/2010 |
| WO | 2011105109 A1 | 9/2011 |
| WO | 2011106663 A1 | 9/2011 |
| WO | 2012014436 A1 | 2/2012 |
| WO | 2012/170781 A1 | 12/2012 |
| WO | 2014004439 A1 | 1/2014 |
| WO | 2014/093310 A1 | 6/2014 |
| WO | 2015174895 A1 | 11/2015 |
| WO | 2016065000 A1 | 4/2016 |
| WO | 2016/103873 A1 | 6/2016 |
| WO | 2016147760 A1 | 9/2016 |
| WO | 2016189759 A1 | 12/2016 |
| WO | 2017053035 A1 | 3/2017 |
| WO | 2017053036 A1 | 3/2017 |
| WO | 2017189151 A1 | 11/2017 |
| WO | 2017189152 A1 | 11/2017 |
| WO | 2018006027 A1 | 1/2018 |
| WO | 2018210751 A1 | 11/2018 |
| WO | 2018210752 A1 | 11/2018 |
| WO | 2018210753 A1 | 11/2018 |
| WO | 2018210754 A1 | 11/2018 |
| WO | 2018210756 A1 | 11/2018 |
| WO | 2018210757 A1 | 11/2018 |
| WO | 2018210758 A1 | 11/2018 |
| WO | 2019005666 A1 | 1/2019 |
| WO | 2019/026354 A1 | 2/2019 |
| WO | 2019048397 A1 | 3/2019 |
| WO | 2019125227 A1 | 6/2019 |
| WO | 2019125228 A1 | 6/2019 |
| WO | 2021/015654 A1 | 1/2021 |

(56) References Cited

FOREIGN PATENT DOCUMENTS

OTHER PUBLICATIONS

Extended European Search Report dated Jul. 26, 2021, issued by the European Patent Office in corresponding European Application No. 17935141.6-1102, (7 pages).
Extended European Search Report dated Oct. 1, 2021, issued by the European Patent Office in corresponding European Application No. 18892993.9-1102, (6 pages).
Office Action (Examination Report No. 1 for standard patent application) dated Jul. 6, 2020 by the Australian Government—IP Australia in corresponding Australian Patent Application No. 2017443955. (4 pages).
Office Action (Notice of Reason(s) for Rejection) dated Jun. 29, 2021, by the Japanese Patent Office in Corresponding Japanese Patent Application No. 2020-534608, and an English Translation of the Office Action. (13 pages).
Office Action (Notice of Reasons for Rejection) dated Aug. 23, 2021, by the Japanese Patent Office in corresponding Japanese Patent Application No. 2020-534555, and an English Translation of the Office Action. (23 pages).
Office Action (Notice of Reasons for Rejection) dated May 17, 2021, by the Japanese Patent Office in corresponding Japanese Patent Application No. 2020-527920, and an English Translation of the Office Action. (13 pages).
Office Action (Notice of Reasons for Rejection) dated Oct. 4, 2021, by the Japanese Patent Office in corresponding Japanese Patent Application No. 2020-527920, and an English Translation of the Office Action. (12 pages).
Office Action (Notification of the First Office Action) dated May 14, 2021 by the China National Intellectual Property Administration (CNIPA) of the People's Republic of China in corresponding Chinese Patent Application No. 201780096156.6, and an English Translation of the Office Action. (29 pages).
Office Action (Notification of the First Office Action) dated May 6, 2021 by the China National Intellectual Property Administration (CNIPA) of the People's Republic of China in corresponding Chinese Patent Application No. 201880080005.6, and an English Translation of the Office Action. (16 pages).
Office Action dated Dec. 24, 2020, by the Federal Service for Intellectual Property in Russian Patent Application No. 2020114949/03(024818) and an English Translation of the Office Action. (14 pages).
Office Action dated Jan. 18, 2022 by the Columbian Patent Office for Application No. NC2020/0006671 (18 pages).
Office Action dated Oct. 27, 2021, by the Colombian Patent Office in Colombian Patent Application No. NC2020/0004955 and an English Translation of the Office Action. (19 pages).
Office Action dated Oct. 5, 2021, by the Japanese Patent Office in corresponding Japanese Patent Applicatior No. 2020-534608, and an English Translation of the Office Action. (11 pages).
Office Action dated Dec. 30, 2020, by the Federal Service for Intellectual Property in Russian Patent Application No. 2020123962/03(041374) and an English Translation of the Office Action. (12 pages).
Office Action (Notification of the First Office Action) dated Dec. 8, 2020 by the China National Intellectual Property Administration (CNIPA) of the People's Republic of China in corresponding Chinese Patent Application No. 201880079974.X, and an English Translation of the Office Action. (18 pages).
Office Action (Notification of the Second Office Action) dated Oct. 26, 2021 by the China National Intellectual Property Administration (CNIPA) of the People's Republic of China in corresponding Chinese Patent Application No. 201780096146.2 and an English Translation of the Office Action. (10 pages).
Office Action (Notice of Reason(s) for Rejection) dated Jun. 29, 2021, by the Japanese Patent Office in corresponding Japanese Patent Application No. 2020-534618, and an English Translation of the Office Action. (9 pages).
Extended European Search Report dated Jul. 2, 2021, issued by the European Patent Office in corresponding European Application No. 17935361.0-1102, (8 pages).
International Search Report (PCT/ISA/210) and Written Opinion (PCT/ISA/237) dated Oct. 10, 2018, by the Swedish Patent Office as the International Searching Authority for International Application No. PCT/SE2018/050383.
International Search Report (PCT/ISA/210) and Written Opinion (PCT/ISA/237) dated Mar. 1, 2019, by the Swedish Patent Office as the International Searching Authority for International Application No. PCT/SE2018/051361.
Office Action (Notification of the First Office Action) dated Apr. 29, 2021 by the China National Intellectual Property Administration (CNIPA) of the People's Republic of China in corresponding Chinese Patent Application No. 201780096146.2, and an English Translation of the Office Action. (17 pages).
Office Action (Decision on Grant) dated Nov. 23, 2020, by the Federal Service for Intellectual Property in Russian Patent Application No. 2020123924/03(041325) and an English Translation of the Office Action. (27 pages).
Office Action (Notification of the First Office Action) dated Oct. 19, 2020, by the China National Intellectual Property Administration (CNIPA) of the People's Republic of China in corresponding Chinese Patent Application No. 201780096125.0, and an English Translation of the Office Action. (14 pages).
Office Action (Notice of acceptance for patent application) dated Nov. 9, 2020 by the Australian Government—IP Australia in corresponding Australian Patent Application No. 2017443955. (3 pages).
Office Action (Decision on Grant) dated Sep. 28, 2020, by the Federal Service for Intellectual Property in Russian Patent Application No. 2020123912/03(041313) and an English Translation of the Office Action. (25 pages).
Office Action (Notification of the First Office Action) dated Nov. 13, 2020, by the China National Intellectual Property Administration (CNIPA) of the People's Republic of China in corresponding Chinese Patent Application No. 201780096151.3, and an English Translation of the Office Action. (9 pages).
Office Action (Notification of the First Office Action) dated Oct. 20, 2020, by the China National Intellectual Property Administration (CNIPA) of the People's Republic of China in corresponding Chinese Patent Application No. 201780096152.8, and an English Translation of the Office Action. (20 pages).
International Search Report (PCT/ISA/210) dated Oct. 10, 2018, by the Swedish Patent Office as the International Searching Authority for International Application No. PCT/SE2017/000053.
International Search Report (PCT/ISA/210) dated Oct. 10, 2018, by the Swedish Patent Office as the International Searching Authority for International Application No. PCT/SE2017/000055.
International Search Report (PCT/ISA/210) dated Sep. 3, 2018, by the Swedish Patent Office as the International Searching Authority for International Application No. PCT/SE2017/000050.
International Search Report (PCT/ISA/210) dated Sep. 3, 2018, by the Swedish Patent Office as the International Searching Authority for International Application No. PCT/SE2017/000051.
International Search Report (PCT/ISA/210) dated Sep. 3, 2018, by the Swedish Patent Office as the International Searching Authority for International Application No. PCT/SE2017/000054.
International Search Report (PCT/ISA/210) dated Sep. 7, 2018, by the Swedish Patent Office as the International Searching Authority for International Application No. PCT/SE2017/000052.
Written Opinion (PCT/ISA/237) dated Oct. 10, 2018, by the Swedish Patent Office as the International Searching Authority for International Application No. PCT/SE2017/000053.
Written Opinion (PCT/ISA/237) dated Oct. 10, 2018, by the Swedish Patent Office as the International Searching Authority for International Application No. PCT/SE2017/000055.
Written Opinion (PCT/ISA/237) dated Sep. 3, 2018, by the Swedish Patent Office as the International Searching Authority for International Application No. PCT/SE2017/000050.
Written Opinion (PCT/ISA/237) dated Sep. 3, 2018, by the Swedish Patent Office as the International Searching Authority for International Application No. PCT/SE2017/000051.

(56) References Cited

OTHER PUBLICATIONS

Written Opinion (PCT/ISA/237) dated Sep. 3, 2018, by the Swedish Patent Office as the International Searching Authority for International Application No. PCT/SE2017/000054.

Written Opinion (PCT/ISA/237) dated Sep. 7, 2018, by the Swedish Patent Office as the International Searching Authority for International Application No. PCT/SE2017/000052.

Third Party Observation mailed on Apr. 7, 2020, by the Swedish Patent Office for International Application No. PCT/SE2017/000050.

Third Party Observation mailed on Apr. 2, 2020, by the Swedish Patent Office for International Application No. PCT/SE2017/000051.

Office Action dated Sep. 30, 2022, by the U.S. Patent and Trademark Office in U.S. Appl. No. 16/757,926.

Office Action (Decision to Grant a Patent) dated Sep. 13, 2022, by the Japanese Patent Office in corresponding Japanese Patent Application No. 2020-534618, and an English Translation of the Office Action. (5 pages).

\* cited by examiner

ABSORBENT ARTICLE AND METHOD FOR MANUFACTURING AN ABSORBENT ARTICLE

TECHNICAL FIELD

The disclosure relates to an absorbent article comprising an absorbent core sandwiched between a liquid-permeable topsheet and a liquid-impermeable backsheet. The disclosure also relates to an absorbent core for an absorbent article, and a method for manufacturing an absorbent article of the above-mentioned type.

BACKGROUND

Wearable and disposable absorbent articles, for example in the form of diapers, incontinence garments, feminine garments and the like, are well known. Such articles are used to absorb, distribute and store various types of body exudates while providing a high level of comfort and sense of dryness to the wearer during use.

A conventional disposable absorbent article in the form of a diaper is normally designed with an absorbent core which is sandwiched between a topsheet and a backsheet. The article is arranged along a longitudinal axis and along a transversal axis which extends in a perpendicular direction in relation to the longitudinal axis. Furthermore, the article can be divided into a front portion, a back portion and a crotch portion.

The absorbent article will absorb body exudates when it is worn. A potential disadvantage which may occur when the absorbent article is in its wet condition is that the crotch portion may sag and hang down. This tendency for sagging is unwanted and may lead to insufficient comfort, fit and function of the article.

A previously known absorbent article of the above-mentioned kind is disclosed in the patent document US 2012/316528. This document shows a disposable diaper having an absorbent core which, according to an embodiment, comprises longitudinally extending channels. The purpose of the diaper is to provide good liquid handling properties and an increased flexibility and improved fit during use.

Even though the article disclosed in US 2012/316528 fulfills certain requirements related to liquid handling and fit, there is still a need for further improvements.

SUMMARY

The present disclosure is based on the insight that the ability of an absorbent article such as for example a diaper, to avoid sagging in its wet condition during use, may be influenced by certain features of the article.

In accordance with the invention, there is provided an absorbent article, an absorbent core, and a method for manufacturing an absorbent article.

There is provided an absorbent article comprising an absorbent core sandwiched between a liquid-permeable topsheet and a liquid-impermeable backsheet, said article being arranged along a longitudinal axis and a transversal axis extending in a perpendicular direction in relation to the longitudinal axis and said article defining a front portion, a back portion and a crotch portion, wherein said absorbent core comprises an absorbent component enclosed by a core cover comprising an upper side and a lower side, and a sealing arrangement for joining said upper and lower sides, and comprising two channel sealings in said crotch portion defining a first channel sealing width and a second channel sealing width. Furthermore, the channel sealings are formed by thermo and/or mechanical welding pattern.

The welding pattern may comprise a plurality of welding spots being arranged in the form of a first row along the longitudinal axis wherein each welding spot extends along a first axis, being different from the longitudinal axis. Furthermore, a plurality of welding spots being arranged in the form of a second row along the longitudinal axis wherein each welding spot in the second row extends along a second axis, also being different from the longitudinal axis, and said first axis and second axis may define a first angle ($\alpha 1$) in relation to each other.

The disclosure provides certain advantages. The disclosure fulfills requirements on absorbent articles related to improved fit, comfort and function during use, especially in its wet condition. Also, due to the above-mentioned thermo and/or mechanical welding pattern, there is provided an absorbent article with channel sealings which present sufficient sealing strength in both its longitudinal and transversal direction. In this manner, high demands during wear and handling of such an absorbent article may be obtained. By the present disclosure in claim 1, a sealing strength which is sufficient for a demanding use of the article is obtained so that the article maintains its sealing strength also in its wet condition. Also, the disclosure is based on the insight that the article can be produced with a high level of sealing strength in both its longitudinal and transversal direction.

The channel sealings, comprising a plurality of welding spots being arranged in the form of a first row along the longitudinal axis and a second row also along the longitudinal axis, may be generally parallel to said longitudinal axis. Both the first row and the second row of the plurality of welding spots may be generally parallell to said longitudinal axis.

Said channel sealings may also be generally straight.

The thermo and/or mechanical welding pattern may be formed by thermo-sealing or ultrasonic welding.

The absorbent article may be arranged so that said first angle ($\alpha 1$) is 45-130°, 45-100° or 45-70°.

Each welding spot has a length and a width and the length is greater than the width. The length may be at least 1.1, or 1.2 greater than the width. Each welding spot, in the first row, extends in its length direction along a first axis, and each welding spot, in the second row, extends along a second axis. Said first axis and second axis defining a first angle ($\alpha 1$) in relation to each other.

Said welding spots may be generally rectangular, oval or oblong.

The length of each welding spot may be 1-6 mm, or 1.5-4.5 mm. The width of each welding spot may be 0.5-3.0 mm or 0.8-1.2 mm. The distance between two adjacent welding spots in the longitudinal direction of the article may be 1-5 mm, measured from the centre point of each welding spot. The distance between two adjacent welding spots, measured from the end edge of each welding spot, may not be less than 0.5 mm.

Said first axis may define a second angle with reference to said longitudinal axis which is within the interval 30-60°.

The absorbent article may comprise two side seams along the sides of said core.

The core cover may be formed by a separate upper core cover layer and a separate lower core cover. However, the disclosure is not limited to a core cover comprising two separate core cover layers. The core cover may also be of one single material layer. The absorbent component may be enclosed by one core cover layer folded in two, or enclosed by a continuous core cover sheet, thereby providing upper and lower core cover sides for wrapping the absorbent component. The core cover may be made of thermoplastic polymer material fibers or filaments. The core cover may be made of nonwoven material. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The core cover may be configured with a basis weight which is in the interval 5-20 g/m$^2$.

A centre segment having a first width, a1 may be defined in the absorbent component between the channel sealings, and two side segments each having a second width, a2, may be defined in the absorbent component outside each channel sealing.

The total weight of the absorbent material in the centre segment may generally be equal to, or greater than, the total weight of the absorbent material in each one of the side segments.

A third width, b1, may be defined between the channel sealings and a fourth width, b2, may be defined between a channel sealing and a side seam, and the ratio of the first width and the third width may be greater than the ratio of the second width and the fourth width.

The absorbent article may be configured so that 33-41 weight % of the total amount of absorbent material in the absorbent component in the crotch portion is in the centre segment and 25-33 weight % of the total absorbent material in the absorbent component in the crotch portion is in each one of the side segments.

The absorbent material in said crotch portion may comprise pulp material and superabsorbent material, said pulp material having a basis weight which is in the interval of 50-400 g/m$^2$ and said superabsorbent material having a basis weight which is in the interval of 100-900 g/m$^2$.

The ratio of the first width (a1) and the third width (b1) may be in the interval 0.75-0.91, such as 0.80-0.86 and the ratio of the second width (a2) and the fourth width (b2) may be in the interval 0.57-0.71, such as 0.62-0.66.

Said first, second, third and fourth widths (a1, a2, b1, b2) may be configured so that b1<b2*2 and a1<a2*2.

The side seams may be formed by a thermo and/or mechanical welding pattern arranged in the form of a single row of welding spots in said crotch portion and in the form of three rows of welding spots outside said crotch portion. The welding pattern may be formed by thermo-sealing or ultrasonic welding.

The channel sealings may define a first effective channel sealing width and a second effective channel sealing width, respectively, and the side seams may define a third and fourth effective width, respectively, along said crotch portion and may define a fifth and sixth effective width, respectively, along said front portion and back portion; said effective widths being defined as the extension of said sealing arrangement in the transverse direction of the article, along any cross-section of the crotch portion.

The sum of said first to sixth effective widths in the transversal direction may be generally constant along said core.

Said absorbent component may comprise absorbent material with a basis weight which is within the interval 400-700 g/m$^2$ and having a maximum deviation of ±5% of said basis weight.

Said channel sealings may be generally straight. Also, said channel sealings may be generally parallel to said longitudinal axis.

There is also provided an absorbent core for an absorbent article, said absorbent core comprising an absorbent component enclosed by a core cover comprising an upper and a lower side, and a sealing arrangement for joining said upper and lower sides and comprising two channel sealings defining, in a crotch portion, a first channel sealing width and a second channel sealing width. Furthermore, the channel sealings are formed by thermo and/or mechanical welding pattern comprising a plurality of welding spots being arranged in the form of a first row along the longitudinal axis in which each welding spot extends along a first axis, and a second row along the longitudinal axis in which each welding spot extends along a second axis, said first axis and second axis defining a first angle ($\alpha$1) in relation to each other.

There is also provided a method for manufacturing an absorbent article comprising a longitudinal axis and a transversal axis extending in a perpendicular direction in relation to the longitudinal axis and said article comprising a front portion, a back portion and a crotch portion, comprising: forming an absorbent core with an absorbent component and enclosing said absorbent component by a core cover comprising an upper side and a lower side; providing two channel sealings positioned in the crotch portion joining said upper and lower core sides; and sandwiching said absorbent core between a liquid-permeable topsheet and a liquid-impermeable backsheet. Furthermore, method comprises: forming said channel sealings by a thermo and/or mechanical welding pattern comprising a plurality of welding spots being arranged in the form of a first row along the longitudinal axis in which each welding spot extends along a first axis, and a second row along the longitudinal axis in which each welding spot extends along a second axis, forming said first axis and second axis so that they define a first angle ($\alpha$1) in relation to each other.

Further advantages and advantageous features of the disclosure are disclosed in the following description and in the dependent claims.

BRIEF DESCRIPTION OF THE DRAWINGS

The disclosure will be described in greater detail below with reference to the figures shown in the appended drawings.

DETAILED DESCRIPTION

Different aspects of the present disclosure will be described more fully hereinafter with reference to the enclosed drawings. The embodiments disclosed herein can, however, be realized in many different forms and should not be construed as being limited to the aspects set forth herein.

Figure 1:
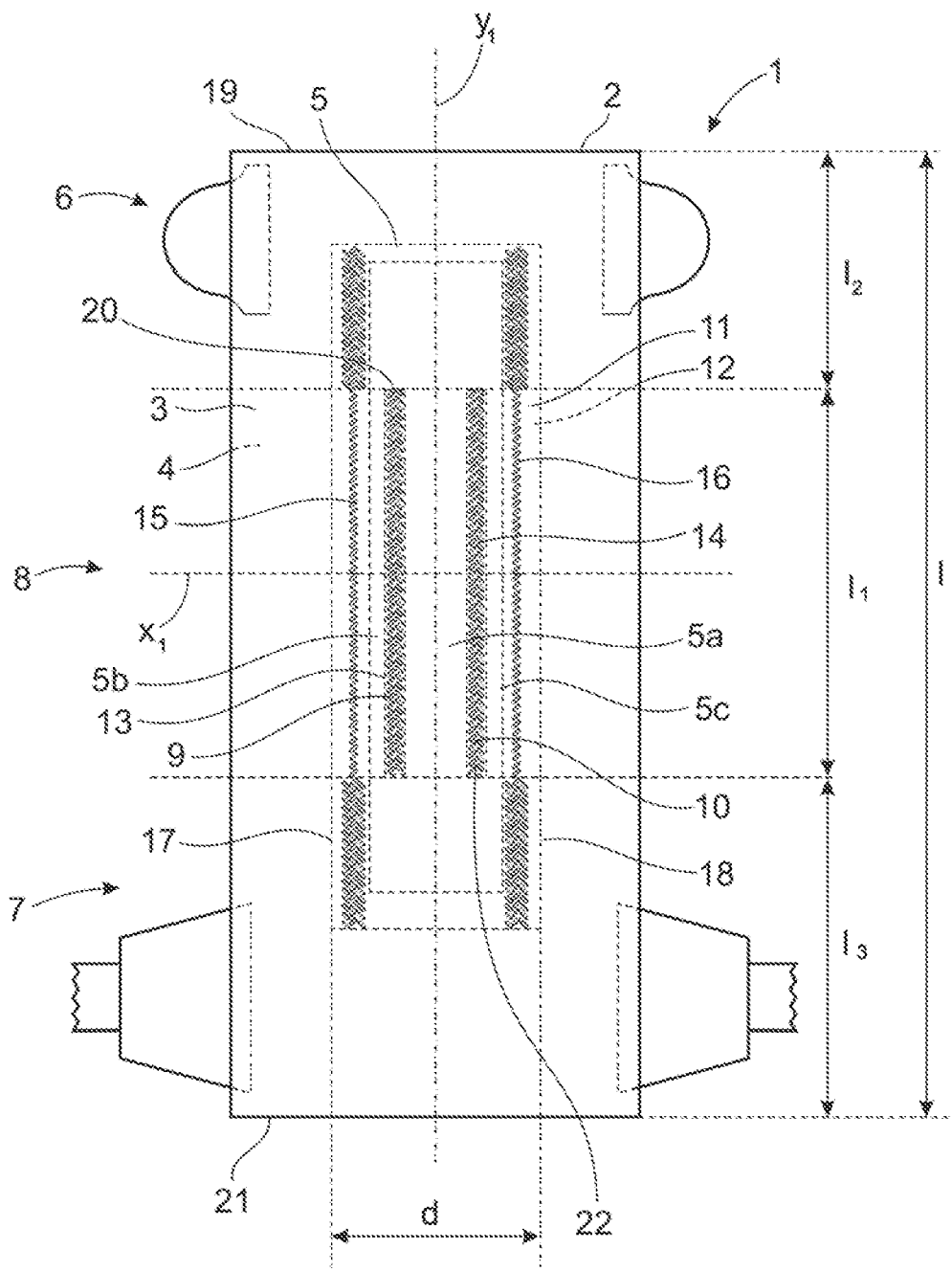
FIG. 1 shows a view from above of an absorbent article in the form of a diaper.

With initial reference to FIG. 1, there is shown a view from above of an absorbent article 1 in the form of a baby diaper. The absorbent article 1 is shown in FIG. 1 in an unfolded and flat state. Also, the absorbent article 1 is based on an absorbent structure for absorbing body exudates from a wearer to provide a dry and comfortable fit for the wearer.

As shown in FIG. 1, the absorbent article 1 comprises a liquid-permeable topsheet 3, a liquid-impermeable backsheet 4 an absorbent core 5 which is sandwiched between the topsheet 3 and the backsheet 4. The topsheet 3 is arranged at the surface of the article 1, i.e. at the side which is facing the wearer, whereas the backsheet 4 is arranged at the underside of the article 1. Furthermore, both the topsheet 3 and the backsheet 4 extend laterally outside of the absorbent core 5 along the entire perimeter of the article 1.

The absorbent core shown in FIG. 1 has a generally rectangular design. However, the disclosure is not limited to this design but can be formed in generally any geometric form within the scope of the disclosure.

The topsheet 3, backsheet 4 and the absorbent core 5 may consist of any materials suitable for their purpose, as will be discussed in further detail below.

As shown in FIG. 1, the absorbent article 1 has a longitudinal extension along a longitudinal axis y1 and a transverse extension along a transverse axis x1, which is perpendicular to the longitudinal axis y1. Furthermore, the absorbent article 1 can be defined as being divided into a front portion 6, a back portion 7 and a crotch portion 8. The front 6 and back portions each having a waist edge 2. The front portion 6 is intended to be oriented in a direction towards the wearer's belly during use of the article 1.

Figure 2:
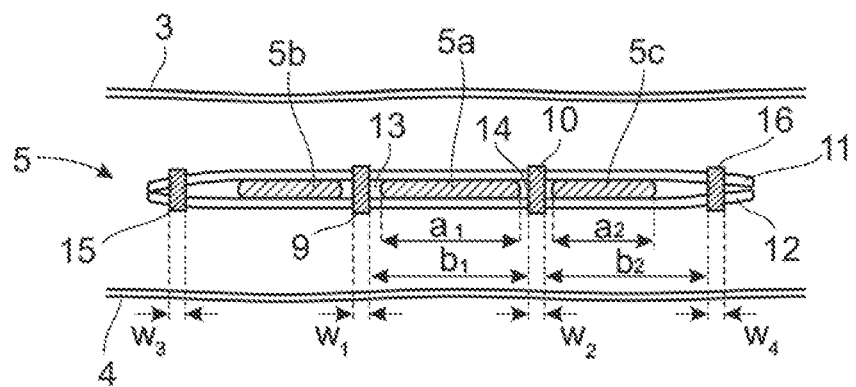
FIG. 2 shows a cross-sectional view of the diaper.

Furthermore, with reference to FIGS. 1 and 2, wherein FIG. 2 is a cross-sectional view of the absorbent article 1 along the transversal axis x1, it should be noted that the absorbent core 5 comprises an absorbent component 5a, 5b, 5c which is enclosed by a core cover comprising an upper side 11 and a lower side 12, and is formed with two longitudinally extending and generally straight channel sealings 9, 10 which are configured so as to join the upper side 11 to the lower side 12, see in particular FIG. 2, wherein the absorbent component 5a, 5b, 5c is sandwiched between said upper side 11 and said lower side 12. According to FIGS. 1 and 2, the core cover is formed by a separate upper core cover layer and a separate lower core cover layer. However, the disclosure is not limited to a core cover comprising two separate material layers. The core cover may also be of one single material layer. The absorbent component may be enclosed by one core cover layer folded in two, or enclosed by a continuous core cover sheet, thereby providing upper and lower core cover sides for wrapping the absorbent component.

The upper side 11 and the lower side 12 is attached to each other by thermo and/or mechanical bonding, such as thermo-sealing or ultrasonic welding. The attachment may also comprise adhesive bonding, stitching or the like, or combinations of the same. According to the embodiment shown in FIGS. 1 and 2, the upper side 11 and the lower side 12 are attached to each other by ultrasonic welding.

The channel sealings 9, 10 are positioned along two corresponding channels 13, 14 which constitute sections of the absorbent core 5 which are not filled with absorbent material. This is obtained through manufacturing the absorbent core 5 involving a mat forming process during which absorbent material is omitted from the areas which correspond to the channels 13, 14. In this manner, no absorbent material will be present in the channels 13, 14, i.e. where the channel sealings 9, 10 are arranged.

As shown in FIGS. 1 and 2, the absorbent core 5 may be divided into a centre segment 5a and two side segments 5b, 5c in the crotch portion 8. The two above-mentioned channels 13, 14, and the channel sealings 9, 10 will consequently be configured so that they separate the three segments 5a, 5b, 5c from each other along the crotch area 8. Also, the length l1 of each channel sealing 9, 10 may correspond to the length of the crotch portion 8 and may also be slightly less than the length of each channel 13, 14.

The absorbent core 5 may be generally rectangular and comprise two generally straight channel sealings 9, 10 which are generally parallel to said longitudinal axis y1 and define a first channel sealing width w1 and a second channel sealing width w2. The disclosure is not limited to a rectangular core 5 and generally straight channel sealings 9, 10, i.e. other geometrical configurations may occur. The channel sealings 9, 10 are positioned within the first channel 13 and the second channel 14, respectively, and are configured to attach the upper side 11 to the lower side 12.

Furthermore, the centre segment 5a is defined in the core 5 between the channel sealings 9, 10. Also, the two side segments 5b, 5c are defined in the core 5 outside each channel sealing 9, 10. More precisely, the first side segment 5b is positioned between the first channel sealing 9 and a first side seam 15, whereas the second side segment 5c is positioned between the second channel sealing 10 and a second side seam 16. The side seams 15, 16 are configured for joining the upper core cover side 11 to the lower side 12, suitably by means of ultrasonic welding or other relevant technologies as described above with reference to the channel sealings 9, 10. Furthermore, the side seams 15, 16 extend along each side of the absorbent core 5, along a first side edge 17 and a second side edge 18 of the absorbent core 5.

As mentioned, the length l1 of the crotch portion 8 may be equal to the length of the channel sealings 9, 10, i.e. the channel sealings 9, 10 may extend along the crotch portion 8 only. However, the side seams 15, 16 may not just be positioned along the crotch portion 8 but also extend along the front portion 6 and the back portion 7. This will be described in detail below.

In summary, the absorbent core 5 is formed with a sealing arrangement which is constituted by the two channel sealings 9, 10 and the two side seams 15, 16. The sealing arrangement is configured so that, in the crotch portion 8, the absorbent core 5 is divided into a centre segment 5a and two side segments 5b, 5c. More precisely, and as shown in FIG. 2, the centre segment 5a has a first width a1 and each side segment 5b, 5c has a second width a2. Also, a third width b1 is defined between the two channel sealings 9, 10. Furthermore, a fourth width b2 is defined between the first channel sealing 9 and the first side seam 15, and between the second channel sealing 10 and the second side seam 16.

According to FIGS. 1 and 2, the absorbent component 5a, 5b 5c is configured so that the weight of absorbent material of the centre segment 5a is generally equal to or greater than the weight of absorbent material in each one of the side segments 5b, 5c. As will be described in greater detail below, the absorbent material may comprise a mixture of pulp material and superabsorbent material. Also, the ratio of the first width a1 and the third width b1 is greater than the ratio of the second width a2 and the fourth width b2. In practical terms, this means that the available space for the absorbent material to expand in the centre segment 5a, during use of the absorbent article 1, is less than the corresponding available space for each side segment 5b, 5c. This will lead to a situation in which the centre segment 5a will be stiffer (in its wet condition) than the side segments 5b, 5c. This means that any tendency in the crotch portion 8 of the absorbent article 1 to sag will be reduced.

The expression "generally equal" as used above for describing the weight of absorbent material in the centre segment 5a as compared with the side segments 5b, 5c should be interpreted in a manner wherein the weight of absorbent material could have a variation of approximately ±5 weight % in any part of the crotch portion 8.

The absorbent component 5*a*,5*b*,5*c* in the crotch portion may be configured so that 33-41 weight % of the absorbent material is in the centre segment 5*a*, whereas 25-33 weight % of the absorbent material is in each one of the side segments 5*b*, 5*c*. In this manner, the desired stiffness in the centre segment 5*a* may be obtained.

In summary, the absorbent core 5 comprises an absorbent component which in turn comprises the three above-mentioned segments 5*a*, 5*b*, 5*c* in the crotch portion 8 of the absorbent article 1. In the crotch portion 8, the absorbent component 5*a*, 5*b*, 5*c* comprises absorbent material which may be in the form of pulp material and superabsorbent material. The pulp material may have a basis weight which is in the interval of 50-400 $g/m^2$ and the superabsorbent material may have a basis weight which is in the interval of 100-900 $g/m^2$. However, a deviation of ±5% of the chosen basis weight in the crotch portion 8 is accepted.

Various types of materials may be used for the absorbent article 1. The topsheet 3 is arranged to face the wearer of the absorbent article 1 when worn. The topsheet 3 may be formed by a fluid permeable nonwoven fabric or film which is made of thermoplastic synthetic fibers. The topsheet 3 may be sufficiently liquid-permeable to allow discharged body fluids to penetrate through the thickness of the topsheet 3. Also, the topsheet 3 may be suitably manufactured from a material which is compliant and soft-feeling to the skin of the wearer. The topsheet 3 may consist of a single layer or have a laminate structure comprising a plurality of layers, for example, two or more layers. The layers may be made of the same material, or some, or all the layers, may be made of different materials.

The layer of the topsheet 3 or, for the case of a laminate structure, one, some or all the layers of the topsheet may be made of a single material or have plural portions made of different materials, e.g., within different parts of the wearer-facing surface of the topsheet.

The layer of the topsheet 3 or, for the case of a laminate structure, one, some or all of the layers of the topsheet may be a nonwoven material, a perforated plastic film, a plastic or textile mesh, or a liquid permeable foam layer.

The layer of the topsheet 3 or, for the case of a laminate structure, one, some or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers.

The topsheet may have a basis weight in the range of 8-40 $g/m^2$. However, the disclosure is not limited to topsheets having this basis weight only.

Furthermore, the backsheet 4 may be constituted by a liquid-impermeable and breathable layer such as a polymeric film, for example a film of polyethylene or polypropylene. According to different embodiments, the materials which may be used for the backsheet 4 include thin and flexible fluid impermeable plastic films, or fluid impermeable nonwoven materials, fluid impermeable foams and fluid impermeable laminates.

The backsheet 4 may be formed by a single layer, but may alternatively be formed by a multi-layered structure, i.e. a laminate, wherein at least one layer is fluid impermeable. Furthermore, the backsheet 4 may be elastic in any direction.

Furthermore, the backsheet 4 may have a laminate structure comprising a liquid barrier sheet and a nonwoven layer arranged on top of each other (not shown in detail in the drawings), wherein the nonwoven layer is arranged at an outer side away from the wearer of the absorbent article 1 when worn. The nonwoven layer may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The nonwoven layer may have a basis weight in the range of 5-40 $g/m^2$.

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, such as a thermoplastic film material, allows for a particularly good printability of the liquid barrier sheet. The liquid barrier sheet may also contain paper fibers. The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo-mechanical bonding, such as thermo-sealing, ultrasonic bonding, such as ultrasonic welding, an adhesive or adhesives, stitching or the like. The liquid barrier sheet may be a breathable microporous film. The microporous film may be made of a material comprising at least two basic components, namely a thermoplastic elastomeric polyolefin polymer and a filler. These components and, in some embodiments, additional other components can be mixed together, heated and subsequently extruded into a mono-layer or multi-layer film using any one of various film-producing processes, such as cast embossed, chill and flat cast, and blown film processes.

Regarding the choice of materials for the various layers in the absorbent article, the materials may be chosen for the bonding process to form the channel sealings and side seams. For example, if ultrasonic welding is chosen for joining the upper and lower core cover sides, the chosen materials for the core cover may be adapted to form a secure bond during ultrasonic welding.

Furthermore, the absorbent core 5 is provided between the topsheet 3 and the backsheet 4 to absorb the liquid, such as urine or other bodily fluids, which has passed through the topsheet 3. The absorbent core 5 may be made of one layer only, or of two or more layers. The absorbent core 5 may comprise suitable amounts of superabsorbent particles. Such superabsorbent material is well known in the field of absorbent articles, and is constituted by a water-swellable and water-insoluble material which is capable of absorbing large quantities of fluid upon formation of a hydrogel. The absorbent core 5 may contain superabsorbent material in the form of fibers or particles of absorbent polymer material. For example, the superabsorbent material may be surface cross-linked, partially neutralized polyacrylates.

The superabsorbent material, e.g., the superabsorbent fibers or particles, may be mixed with other absorbent or liquid uptake material or materials, such as cellulose fluff pulp, and/or arranged in pockets or layers in the absorbent core 5. The ratio of superabsorbent material and pulp in the absorbent core 5 may be 0-50 weight % pulp fibers and 50-100 weight % superabsorbent material, or 0-30 weight % pulp fibers and 70-100 weight % superabsorbent material.

The absorbent core 5 may further comprise components for improving the properties of the absorbent core 5. For example, the absorbent core 5 may comprise a binder or binders, such as binder fibers.

The core cover 11,12 may be formed by a separate upper core cover 11 layer and a separate lower core 12 cover. However, the disclosure is not limited to a core cover 11,12 comprising two separate core cover layers. The core cover 11,12 may also be of one single material layer. The absorbent component may be enclosed by one core cover layer folded in two, or enclosed by a continuous core cover sheet, thereby providing upper and lower core cover sides for wrapping the absorbent component. The core cover 11,12 may be made of thermoplastic polymer material fibers or filaments. The core cover 11,12 may be made of nonwoven material. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The core cover may be configured with a basis weight which is in the interval 5-20 g/m².

Furthermore, as known by the skilled person, the various layers of the absorbent article 1 may be attached by means of adhesive material. Such adhesive is not shown in the drawings.

One or more additional layers may be provided in the absorbent article 1. For example, an acquisition layer may be arranged between the absorbent core 4 and the topsheet 3. Such an additional layer may for example be in the form of an airlaid layer, a spunlace layer, a high-loft, foam or any other type of material layer which may be used in an absorbent article to act as a liquid acquisition and absorption layer. The acquisition layer is adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven may be produced with fluff, wood pulp, and here the fluff fibres are dispersed into a fast-moving air stream and condensed onto a moving screen by means of pressure and vacuum.

According to an embodiment, the ratio of the first width a1 of the centre segment 5a and the third width b1, i.e. the distance between the channel sealings 9, 10 (i.e. a1/b1) is in the interval 0.75-0.91, such as 0.80-0.86. Furthermore, the ratio of the second width a2 of each side segment 5b, 5c and the fourth width b2, i.e. the distance between each channel sealing 9, 10 and its corresponding, adjacent side seam 11, 12 (i.e. a2/b2) is in the interval 0.57-0.71, such as 0.62-0.66. In this manner, the required stiffness of the centre segment 5a may be obtained.

In general, the article 1 is arranged so that the ratio of the first width a1 and the third width b1 is greater than the ratio of the second width a2 and the fourth width b2, i.e.

(a1/a1)>(a2/b2)

Furthermore, the first, second, third and fourth widths a1, a2, b1, b2, respectively, may be configured so that:

b1<b2*2 and a1<a2*2

In addition to the arrangement of the first, second, third and fourth widths a1, a2, b1, b2, as described above, the absorbent article 1 is arranged to provide the desired stiffness of the centre segment 5a and the entire absorbent article 1 by the above-mentioned arrangement of the absorbent material in the absorbent core 5. This means that the centre segment 5a is configured for a stiffness in a wet condition which is greater than that of each side segment 5b, 5c. This also means that the absorbent component, i.e. consisting of the centre segment 5a and the side segments 5b, 5c, may be configured with an ability to expand on wetting and to display a first volume in dry condition and a second volume in completely expanded wet condition, the second volume being greater than the first volume.

With reference again to FIG. 1, it can be noted that each channel sealing 9, 10 may have a length l1 which corresponds to the longitudinal extension of the crotch portion 8. Each one of the channel sealings 9, 10 may have a length l1 which is between 5-50%, such as 10-50%, such as between 28-38%, of the total length l of the absorbent article 1. Furthermore, each channel sealing 9, 10 may have a length l1 which is 10-60%, 20-60% or 30-50%, of the length of the absorbent core 5.

A further parameter is the positioning of the channel sealings 9, 10 along the absorbent article 1 in its longitudinal direction. Such positioning may be defined by choosing a suitable value for the distance 12 between the front edge 19 of the article 1 and the front edge 20 of each channel sealing 9, 10. Obviously, this means that decreasing said distance 12 means that the distance 13 between the back edge 21 of the article 1 and the back edge 22 of the channel sealings 9, 10 will be increased, and vice versa.

The position of the channel sealings 9, 10 along the longitudinal direction of the absorbent article 1 may be chosen in a manner so that the distance 12 between the front edge 17 of the article 1 and the front edge 18 of each channel 9, 10 is 15-40% or 22-25%, of the total length l of the article 1.

As mentioned above, the absorbent component 5a, 5b, 5c is enclosed by a core cover comprising an upper side 11 and a lower side 12. The absorbent core 5 may be manufactured as a single layer which is wrapped in nonwoven material and positioned between the topsheet 3 and the backsheet 4 during manufacturing of the absorbent article 1.

Furthermore, the topsheet 3 may comprise at least one additive material such as a skin care composition, at least the surface above the side segments 5b, 5c. This is due to that the side segments 5b, 5c normally will be closest to the body of the wearer of the absorbent article 1. The additive may be located on the parts of the topsheet covering the side segments 5b, 5c.

According to what is known to the skilled person, the absorbent article 1 may additionally be provided with further components such as fastening tabs, elastic elements and other components which are commonly used in absorbent articles such as for example baby diapers or incontinence garments. Such additional components are not described in detail here.

Figure 3:
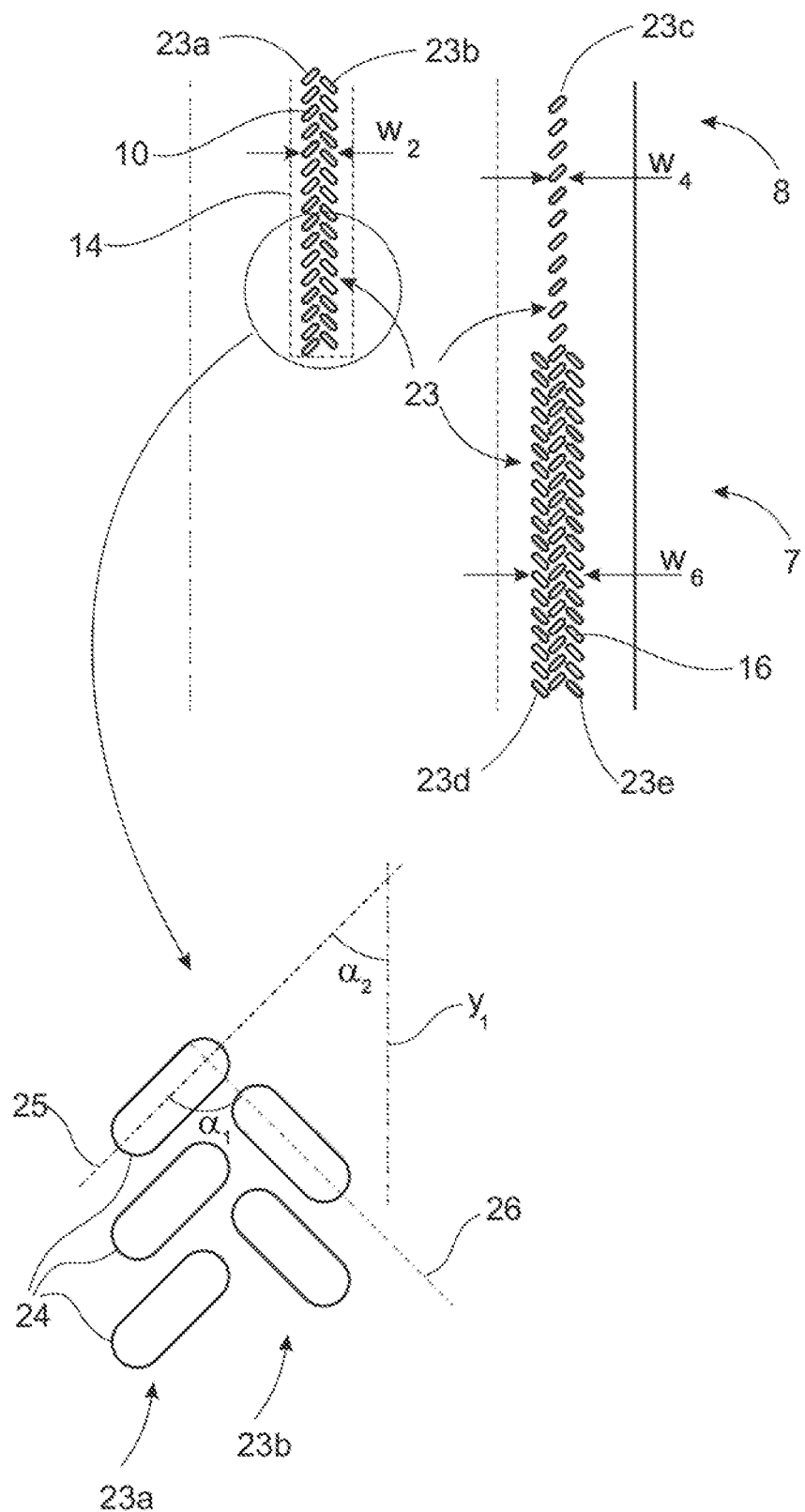
FIG. 3 shows a welding pattern which can be implemented in the disclosure.

With reference to FIGS. 1 and 3, an absorbent core 5 is provided with a sealing arrangement 9, 10, 15, 16, i.e. comprising the above-mentioned channel sealings 9, 10 and the side seams 15, 16. As shown in FIGS. 1 and 3, the side seams 15, 16 extend along the side edges 17, 18 of the core.

The side seams 15,16 may define a first side seam width w3 and a second side seam width w4, respectively, along the crotch portion 8 of the absorbent article 1.

As shown in FIGS. 1 and 3, the channel sealings 9, 10 may be generally straight and generally parallel to the longitudinal axis x1. Also, the side seams 15, 16 may be generally straight and generally parallel to the longitudinal axis x1.

Figure 4:
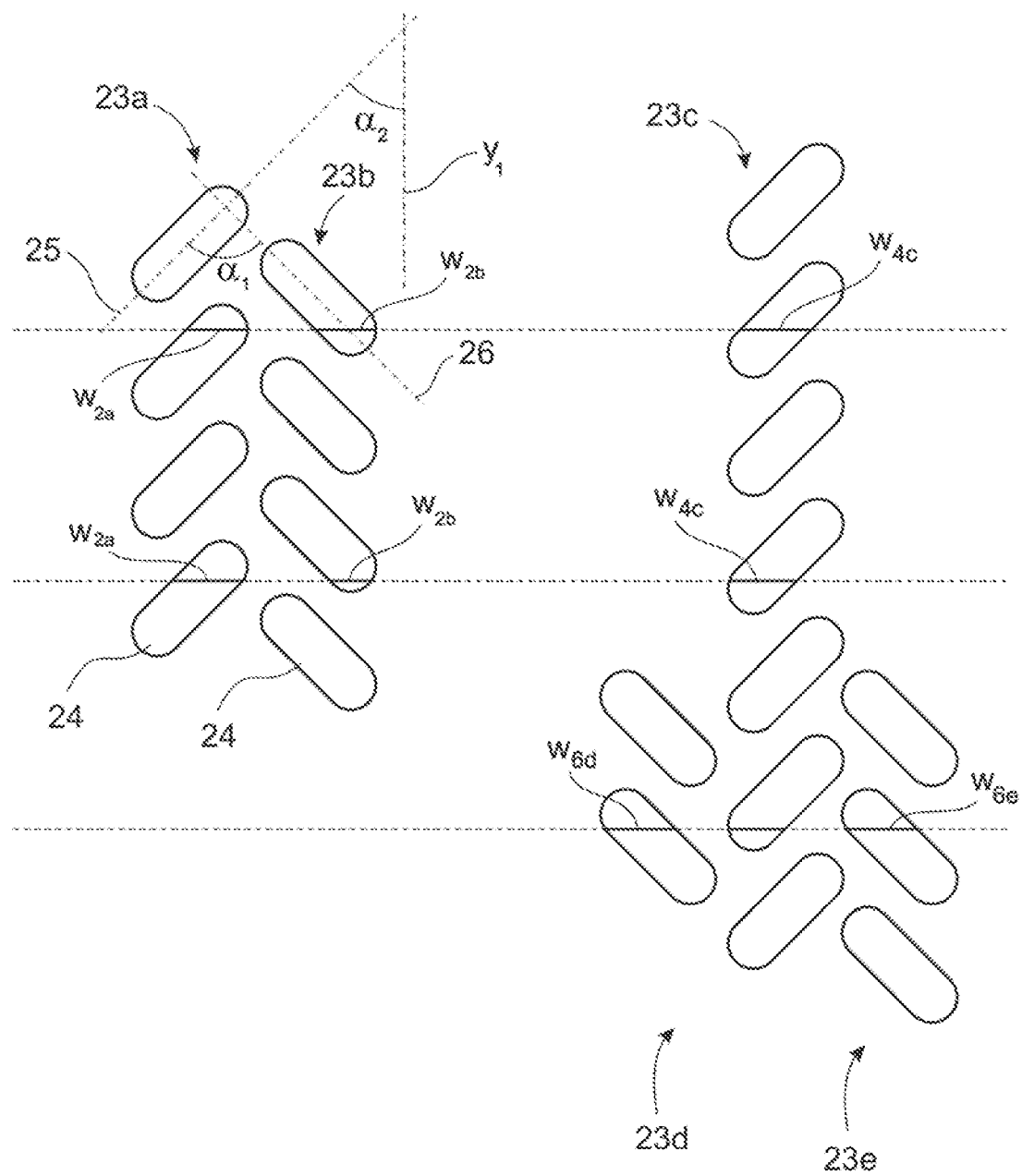
FIG. 4 shows a further view of a welding pattern.

With reference to FIGS. 3 and 4, the sealing arrangement 9, 10, 15, 16 may be constituted by a welding pattern 23 produced by means of a thermo and/or mechanical sealing, such as ultrasonic welding or thermo-sealing. The welding pattern 23 may comprise welding spots 24 which are arranged in the form of a first row 23a in which the welding spots 24 are arranged along a first axis 25. Also, a further number of welding spots 24 are arranged in the form of a second row 23b in which the welding spots 24 extend along a second axis 26. Furthermore, the first axis 25 and the second axis 26 extend in a manner so that they define a first angle $\alpha 1$ in relation to each other. In this manner, it can be ensured that the absorbent core 5 can be manufactured with a high level of sealing strength in both its longitudinal and transversal direction. The strength provided by means of a welding process for producing the channel sealings 9, 10 may be optimized by using the above-mentioned configuration of the welding pattern 23.

Each welding spot has a length and a width and the length may be at least 1.1 or 1.2 greater than the width. The length of each welding spot may be 1-6 mm, or 1.5-4.5 mm. The width of each welding spot may be 0.5-3.0 mm or 0.8-1.2 mm. The welding spots 24 may be of generally rectangular, oval or oblong shape. The distance between two adjacent welding spots in the longitudinal direction of the article may be 1-5 mm, measured from the centre point of each welding spot.

The above-mentioned first angle $\alpha 1$ may be in the interval of 45-130°, 45-100°, or 45-70°. As shown in FIGS. 3 and 4, the first angle $\alpha 1$ may be in the magnitude of 90°.

Also, as shown in FIGS. 3 and 4, the first axis 25 may define an angle $\alpha 2$ with reference to said longitudinal axis y1 which may be within the interval 30-60°.

FIG. 4 teaches one row 23c of welding spots in each side seam 15, 16 along the crotch portion 8, and three rows 23c, 23d, 23e of welding spots in each side seam 15, 16 along the front portion 6 and the back portion 7, respectively. Also, each side seam 15, 16 may define a fifth side seam width w5 and a sixth side seam width w6 along the front portion 6 and back portion 7, respectively.

By using an ultrasonic welding pattern 23 as mentioned above, there is provided an absorbent article 1 with high sealing strength in both its longitudinal and transversal direction. In this manner, high demands during wear and handling of such an absorbent article 1 may be fulfilled.

As shown in FIGS. 3 and 4, the width w2 of the first row 23a and the second row 23b may be defined as an "effective" width in the sense that it is equal to the sum of an effective width w2a of a welding spot 24 in the first row 23a and an effective width w2b of a welding spot 24 in the second row 23b. Each "effective width" can be defined as the length of a welding spot 24 in a transverse direction of the article 1, as indicated in FIG. 4. Similarly, the effective width w4c and w6c, respectively, of the third row 23c of welding spots 24 is also shown in FIG. 4. The effective width of the third row 23c in the crotch portion 8 is the length w4c of a welding spot 24 in said transverse direction, as indicated in FIG. 4. Also, the effective width of the side seam 16 outside the crotch portion 8 (as also indicated in FIG. 1) i.e. the combined effective width of the three rows 23c, 23d, 23e forming the side seam 16 is the sum of the lengths w6c, w6d, w6e in said transverse direction, as shown in FIG. 4.

The sum of the effective channel sealing widths w1, w2 and the first and second side seam widths w3, w4, w5, w6 in a transversal direction of the article 1 may be generally constant along the longitudinal length of the core 5. This is advantageous in a manufacturing process involving ultrasonic welding of the channels sealings 9, 10 and the side seams 15, 16, since the manufacturing process can be arranged so that a generally constant energy transfer is required as the ultrasonic welding of the channels sealings 9, 10 and side seams 15, 16 is produced along the longitudinal direction of the core 5.

A method for manufacturing an absorbent article 1 will now be described. Firstly, the absorbent core 5 is formed by an absorbent component 5a, 5b, 5c which defines the core 5 by enclosing said absorbent component 5a, 5b, 5c between the upper core cover side 11 and the lower core cover side 12. Next, the channel sealings 9, 10 are formed in a manner so that they join the upper side 11 and the lower side 12. As described above, the sealing arrangement 9, 10, 15, 16 may be formed by ultrasonic welding.

Consequently, the absorbent core 5 is formed with an absorbent component 5a, 5b, 5c enclosed between an upper core cover side 11, a lower core cover side 12 and the two channel sealings 9, 10. The upper core cover side 11 and the lower core cover side 12 are joined to define said channel sealings 9, 10.

The absorbent core 5 and the sealing arrangement 9, 10, 14, 15 may be formed in a manner so that the centre segment 5a is formed between the channel sealings 9, 10 and the two side segments 5b, 5c are formed outside each channel sealing 9, 10. More precisely, the centre segment 5a has a first width a1 and each side segment 5b, 5c has a second width a2. Also, the core 5 is formed with a third width b1 between the channel sealings 9, 10 and a fourth width b2 between a channel sealing 9, 10 and a side seam 15, 16.

The article 1 (see FIG. 1) is formed by sandwiching the absorbent core 5 between the liquid-permeable topsheet 3 and the liquid-impermeable backsheet 4. The article 1 defines the longitudinal axis y1 and the transversal axis x1 as described above. Also, the article 1 defines a front portion 6, a back portion 7 and a crotch portion 8. Furthermore, the channel sealings 9, 10 are positioned in the crotch portion 8, i.e. the length l1 of each channel sealing 9, 10 may correspond to the extension of the crotch portion 8.

Furthermore, the channel sealings 9, 10 are formed by an ultrasonic welding pattern 23 which comprises a plurality of welding spots 24 which are arranged in the form of a first row 23a in which the welding spots 24 extend along a first axis 25 and a second row 23b in which the welding spots 24 extend along a second axis 26. Also, the first axis 25 and second axis 26 are formed so that they define the first angle $\alpha 1$ in relation to each other.

The absorbent component 5 may be formed so that the weight of the absorbent material in the centre segment 5a is generally equal to, or greater than, the weight of the absorbent material in each one of the side segments 5b, 5c. Furthermore, the manufacture method may be configured so that the ratio of the first width a1 and the third width b1 is greater than the ratio of the second width a2 and the fourth width b2. This corresponds to the description above with reference to FIGS. 1 and 2.

The disclosure may be varied within the scope of the appended claims. For example, the materials and dimensions used for the different layers forming the absorbent article 1 may be varied, as indicated above. The absorbent article may further include leg elastics, standing gathers, crotch and waist elastics, side panels, fastening systems etc as known to the skilled man in the art and depending of the type of absorbent article intended.

The invention claimed is:

1. An absorbent article comprising an absorbent core sandwiched between a liquid-permeable topsheet and a liquid-impermeable backsheet, said article being arranged along a longitudinal axis and a transversal axis extending in a perpendicular direction in relation to the longitudinal axis and said article defining a front portion, a back portion and a crotch portion,
wherein said absorbent core comprises
an absorbent component enclosed by a core cover comprising an upper side and a lower side, and
a sealing arrangement for joining said upper and lower sides and comprising two channel sealings, a first channel sealing in a first channel and a second channel sealing in a second channel, in said crotch portion, the first channel sealing defining a first channel sealing width and the second channel sealing defining a second channel sealing width,
wherein the channel sealings are each formed by a thermo and/or mechanical welding pattern comprising a plurality of welding spots being arranged in the form of a first row along the longitudinal axis in which each welding spot extends along a first axis, and a second row along the longitudinal axis in which each welding spot extends along a second axis, said first axis and second axis defining a first angle in relation to each other, such that the first axis is not parallel to the second axis,
wherein the sealing arrangement further comprises two side seams along sides of said core,
wherein the channel sealings define a first effective channel sealing width and a second effective channel sealing width, respectively, and wherein the side seams define a third and fourth effective width, respectively, along said crotch portion and define a fifth and sixth effective width, respectively, along said front portion and back portion; said effective widths being defined as an extension of said sealing arrangement in a transverse direction of the article, along any cross-section of the crotch portion,
wherein the sum of said first to sixth effective widths in the transversal direction is generally constant along said core.

2. The absorbent article according to claim 1, wherein the thermo and/or mechanical welding pattern is formed by thermo-sealing or ultrasonic welding.

3. The absorbent article according to claim 1, wherein said first angle is 45-130°.

4. The absorbent article according to claim 1, wherein said welding spots are generally rectangular, oval or oblong.

5. The absorbent article according to claim 1, wherein said first axis defines a second angle with reference to said longitudinal axis which is within the interval 30-60°.

6. The absorbent article according to claim 1, wherein a center segment having a first width is defined in the absorbent component between the channel sealings and two side segments each having a second width are defined in the absorbent component outside each channel sealing.

7. The absorbent article according to claim 6, wherein the absorbent component comprises absorbent material and is formed so that a total weight of absorbent material in the center segment is generally equal to, or greater than, a total weight of absorbent material in each one of the side segments.

8. The absorbent article according to claim 6, wherein a third width is defined between the channel sealings and a fourth width is defined between a channel sealing and a side seam, and wherein the ratio of the first width to the third width is greater than the ratio of the second width to the fourth width.

9. The absorbent article according to claim 6, wherein a crotch portion of the absorbent component comprises absorbent material and the absorbent article is configured so that 33-41 weight % of absorbent material in the absorbent component crotch portion is in the center segment and 25-33 weight % of the absorbent material in the absorbent component crotch portion is in each one of the side segments.

10. The absorbent article according to claim 1, wherein the side seams are formed by an ultrasonic welding pattern arranged in the form of a single row of welding spots in said crotch portion and in the form of three rows of welding spots outside said crotch portion.

11. The absorbent article according to claim 1, wherein said channel sealings are generally straight.

12. The absorbent article according to claim 1, wherein said channel sealings are generally parallel to said longitudinal axis.

13. The absorbent article according to claim 1, wherein said topsheet comprises at least one additive material in the form of a skin care composition.

14. The absorbent article according to claim 1, wherein a length of each welding spot is between 1-6 mm, and/or a width of each welding spot is 0.5-3.0 mm.

15. The absorbent article according to claim 1, wherein a distance between two adjacent welding spots in a longitudinal direction of the article is 1-5 mm, measured from a center point of each welding spot.

16. The absorbent article according to claim 1, wherein a distance between two adjacent welding spots, measured from a nearest edge of each welding spot, is not less than 0.5 mm.

17. An absorbent core for an absorbent article, said absorbent core comprising
an absorbent component enclosed by a core cover comprising an upper and a lower side, the absorbent component defining a front portion, a back portion and a crotch portion, and
a sealing arrangement for joining said upper and lower sides and comprising two channel sealings, a first channel sealing in a first channel and second channel sealing in a second channel, the first channel sealing defining, in the crotch portion, a first channel sealing width and the second channel sealing defining, in the crotch portion, a second channel sealing width,
wherein the channel sealings are each formed by a thermo and/or mechanical welding pattern comprising a plurality of welding spots being arranged in the form of a first row along a longitudinal axis in which each welding spot extends along a first axis, and a second row along the longitudinal axis in which each welding spot extends along a second axis, said first axis and second axis defining a first angle in relation to each other, such that the first axis is not parallel to the second axis,
wherein the sealing arrangement further comprises two side seams along sides of said core,
wherein the channel sealings define a first effective channel sealing width and a second effective channel sealing width, respectively, and wherein the side seams define a third and fourth effective width, respectively, along said crotch portion and define a fifth and sixth effective width, respectively, along said front portion and back portion; said effective widths being defined as an extension of said sealing arrangement in a transverse direction of said core, along any cross-section of the crotch portion, wherein the sum of said first to sixth effective widths in the transversal direction is generally constant along said core.

* * * * *